United States Patent [19]

Bianchi et al.

[11] 4,062,803

[45] Dec. 13, 1977

[54] METHOD FOR THE PREPARATION OF COMPLEXES OF METALS OF THE VIII GROUP OF THE PERIODIC TABLE AND THEIR USE AS CATALYSTS FOR TRANSFERRING HYDROGEN IN A HETEROGENEOUS PHASE

[75] Inventors: Renzo Bianchi, Melegnano; Mario Gabriele Clerici, San Donato Milan, both of Italy

[73] Assignee: ANIC, S.p.A., Palermo, Italy

[21] Appl. No.: 647,781

[22] Filed: Jan. 9, 1976

[30] Foreign Application Priority Data

Jan. 10, 1975 Italy .................................. 19164/75

[51] Int. Cl.$^2$ ............................................. B01J 31/30
[52] U.S. Cl. ............................. 252/429 B; 260/676 R; 260/680 R; 260/596
[58] Field of Search ..................................... 252/429 B

[56] References Cited

U.S. PATENT DOCUMENTS

| | | | |
|---|---|---|---|
| 3,553,181 | 1/1971 | Delbouille et al. | 252/429 B X |
| 3,872,026 | 3/1975 | Dunn | 252/429 B |
| 3,974,095 | 8/1976 | Volpin et al. | 252/429 B X |

OTHER PUBLICATIONS

J. Org. Chem., 28 (July, 1963), pp. 1947–1948.

*Primary Examiner*—Patrick P. Garvin
*Attorney, Agent, or Firm*—James V. Costigan

[57] ABSTRACT

A method is disclosed for preparing complexes of metals of the VIII Group of the Periodic Table, useful as hydrogenation catalysts. The method, as a single-step process, comprises reacting a polymeric complex containing V Group elements and VIII Group metal compounds directly with a metal atom which is directly bound to the V group element in the presence of a reducing substance. The reducing substance is selected among alkali metal and alkaline earth metal hydrides, mixed alkaline-III group element hydrides, organic metallic compounds of III Group metals, alkali metal and alkaline earth metal alkyls, Grignard compounds.

1 Claim, No Drawings

METHOD FOR THE PREPARATION OF COMPLEXES OF METALS OF THE VIII GROUP OF THE PERIODIC TABLE AND THEIR USE AS CATALYSTS FOR TRANSFERRING HYDROGEN IN A HETEROGENEOUS PHASE

This invention relates to a novel method for the preparation of complexes belonging to the VIII Group of the Periodic Table, which can be used as catalysts in hydrogen-transfer reactions in a heterogeneous phase.

The existence of polymeric complexes containing atoms of elements of the V Group and of compounds of transition metals with the atom directly bound to said element are known.

In the case of phosphorus, for example, these complexes are obtained by reacting a polymer containing phosphine radicals grafted to an appropriate compound of the transition metal of interest. The compounds thus obtained can be used as catalysts for hydrogenation, for example of aldehydes, or in olefin carboxylation reactions, but their catalytic activity must be sometimes improved by the presence, in the reaction medium, of an appropriate co-catalyst.

It has been found, and this is a first object of the present invention, that the above mentioned complexes can properly be treated so as to orginate catalyst species which, as employed in heterogeneous phase hydrogen-transfer reactions according to a further object of this invention, have a fair activity. The reactions, as carried out in the presence of such catalysts, evolve towards the formation of the final products with satisfactory conversion yields at a high selectivity, which can be compared with those as obtainable with homogeneous systems, employing, however, the bland operative conditions of these latter but with lesser amount of catalysts.

In addition, the very nature of such catalyst system is such that the end product does not contain any impurity deriving from said systems so that no purification processes are to be resorted to, these processes being sometimes difficult and expensive and having at any rate a certain bearing on the general costs of a process.

The modification reaction of the polymeric complexes according to this invention is carried out by starting from polymeric materials containing in their molecules elements of the V Group directly bound to the transition metal, which are treated with reducing compounds such as alkali metal or alkaline earth metal hydrides, mixed hydrides of said metals with elements of the III Group, organic-metallic derivatives of metals of the III Group of the Periodic Table, alkyl derivatives of alkali metal or alkaline earth metal elements, Grignard derivatives.

Special advantages for the reaction as itself and the subsequent uses thereof have been detected when employing complexes which contain, as the transition metal, iridium, ruthenium, rhodium. The reaction is carried out in an inert atmosphere, at room temperature or slightly above, and in the presence of a solvent which is selected, consistently with the solubility of the reducing compound, among hydrocarbons, ethers, alcohols and others.

Polymeric complexes are thus obtained which have a high activity in the hydrogen-transfer reactions without being compelled concurrently to use any co-catalysts.

Such hydrogen-transfer reactions are carried out according to what has been disclosed in preceding patents of the same applicants, especially Italian Pat. No. 896,393 which relates to the reaction between an acetylene compound and an alcohol, or the Italian Pat. No. 908,842 which relates to the preparation of unsaturated compounds, during progress of which it is possible to employ a single olefin which simultaneously acts both as a hydrogen-donor and a hydrogen acceptor.

Hydrogen-transfer reactions are carried out in the presence of an inert solvent selected among hydrocarbons, either unsubstituted or substituted, aliphatic, aromatic and cycloaliphatic, or in the presence of the reactants only, either in the liquid or the gaseous phase.

The temperature ranges between 50° C and 200° C and all the steps are performed in an inert gas atmosphere.

The foregoing and other operative details will become more clearly apparent in any case from the scrutiny of the following illustrative examples which, however, are nonlimiting to the present invention.

EXAMPLE 1

4.5 grams of a resin as obtained by copolymerization of styrene, p-Br-styrene and divinylbenzene (D. Braum and E. Seelig, Berich. Chem. 1964, 3098-3105) containing 15.9% by weight of Br, are phosphinated, after lithiation with an excess of Li-butyl in benzene, with a slight excess of Cl P (isopropyl)$_2$ and complexed with Ir$^{(III)}$Cl$_3$ in 2-methoxyethanol (Cl% = 4.9; P% = 4.06; Ir% = 10.98). The complexed resin is reduced in a strong excess of NaBH$_4$ in benzene and THF and, after having been separated, washed thoroughly with methanol and water and dried in vacuum, is reacted with a glass microreactor with gaseous pure hexene-1 at a temperature of 140° C at a rate of flow of 1.2 cc an hour. After 30 hours there are obtained 2.217 millimols of dienes and 2.450 millimols of hexane.

Conversion yield 1.7 moles per cycle.

EXAMPLE 2

6 grams of complexed resin prepared as above, containing the following percentage quantities by weight: 6.50; Ir = 10.3% are reduced with LiAlH$_4$ in ethereal solution and reacted under the same reaction conditions as described above.

After 230 hours there are obtained 85.03 millimols of hexadienes and 84.3 millimols of hexane, equivalent to 25 catalytic cycles. Conversion yield 7% in moles per each catalytic cycle.

EXAMPLE 3

0.450 grams of resin, prepared with the same procedure as described above and containing 0.18 millimols of Ir, are reacted with 3 mls of methylbutynol (MBI) and 2 mls isopropanol in a glass autoclave and in an inert atmosphere at a temperature of 80° C. Chromatographic analysis as carried out with a PERKIN ELMER F 11 flame gaschromatograph on CARBOWAX 400 at a temperature of 43° C have given the following results:

| TIME | Millimols of MBI | millimols ACETONE |
|---|---|---|
| 5 hours | 0.237 | 0.310 |
| 11 hours | 0.560 | 0.620 |
| 25 hours | 0.643 | 0.687 |

What we claim is:

1. A method for the preparation of a resin complex of iridium which comprises reacting Ir(III)Cl$_3$ with a copolymer of styrene, p-Br-styrene and divinylbenzene that has been phosphinated with ClP(isopropyl)$_2$ after lithiation with butyl lithium in benzene and said resin complex is reduced with an excess of sodium borohydride.

* * * * *